United States Patent
Wick et al.

(10) Patent No.: US 8,412,464 B1
(45) Date of Patent: Apr. 2, 2013

(54) METHODS FOR DETECTION AND IDENTIFICATION OF CELL TYPE

(75) Inventors: Charles H. Wick, Darlington, MD (US); Michael F. Stanford, Conowingo, MD (US); Alan W. Zulich, Bel Air, MD (US); Samir V. Deshpande, Edgewood, MD (US); Rabih E. Jabbour, Bel Air, MD (US); Jacek P. Dworzanski, Bel Air, MD (US); Patrick E. McCubbin, Baltimore, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/546,282

(22) Filed: Jul. 11, 2012

Related U.S. Application Data

(62) Division of application No. 12/570,038, filed on Sep. 30, 2009, now Pat. No. 8,224,581.

(60) Provisional application No. 61/218,272, filed on Jun. 18, 2009.

(51) Int. Cl.
*G01N 33/48* (2006.01)
*G01N 33/50* (2006.01)

(52) U.S. Cl. .......................................... 702/19; 435/6.14

(58) Field of Classification Search ............. 702/19–23, 702/30; 435/4, 6.14, 6.18; 436/89
See application file for complete search history.

(56) References Cited

U.S. PATENT DOCUMENTS

2003/0139885 A1 * 7/2003 Brock et al. .................... 702/19

* cited by examiner

*Primary Examiner* — John H Le
(74) *Attorney, Agent, or Firm* — Ulysses John Biffoni

(57) ABSTRACT

A process is provided for identifying a cell type in a sample that includes identification of one or more peptide sequences in the sample. Each peptide sequence is assigned to a protein of known sequence. A matrix of assignments is generated for the presence or absence of each peptide in one or more cells. The matrix of assignments is rearranged according to cell classification. A cell type based on the most probable cell classification is identified.

9 Claims, 2 Drawing Sheets

METHODS FOR DETECTION AND IDENTIFICATION OF CELL TYPE

RELATED APPLICATIONS

This Application is a Divisional of application Ser. No. 12/570,038, filed on Sep. 30, 2009, now U.S. Pat. No. 8,224,581, which claimed priority to U.S. Provisional Patent Application Ser. No. 61/218,272 filed on Jun. 18, 2009, which is commonly assigned.

U.S. GOVERNMENT RIGHTS

The invention described herein may be manufactured, used and licensed by or for the U.S. Government.

FIELD OF THE INVENTION

The invention relates generally to a process of identifying a cell in a fluid or solid sample. More specifically, the invention relates to the detection and identification of bacteria, viruses, fungi, or other cellular material in fluid media. Processes are described for rapid and sensitive detection and identification of bacterial organisms in human and animal biological samples as well as environmental samples.

BACKGROUND OF THE INVENTION

Detection and identification of pathogenic microorganisms is an area of high concern in many areas of public health. Particularly important is the identification of pre-existing or newly arising strains of infectious agents such as bacterial, viral, or other disease causing organisms. Diagnostic efforts are hampered by either the total inability or length of time required to identify the presence or absence of a pathogenic organism in the host.

Since the early 2000s, methods of virus and other infectious agent detection have rapidly advanced. A primary detection mechanism for influenza virus, for example, is real-time PCR (RT-PCR) that provides sensitive and relatively rapid identification of a suspected strain of virus. Some of the advantages of RT-PCR are high sensitivity, high specificity, rapid time-to-result, scalability, cost, and quantitative nature. Sample type is less restricted with RT-PCR allowing for lower expense and more rapid viral identification than traditional methods. A severe shortcoming of PCR-based identification techniques is that they require known sequence information for effective detection. For example, RT-PCR uses probes that hybridize to a known sequence. If a significant mutation occurs in a viral target, the known effective probes are rendered useless as they will be unable to hybridize to a mutant sequence. The restricted sequence detection of standard PCR techniques also prevents rapid detection of naturally or intentionally inserted new virulence sequences that may either render the virus or bacteria resistant to therapy, or increase infectivity or transmissibility. Importantly, PCR techniques are unable to detect a previously unknown or unsuspected infectious agent in a sample.

The ability to detect and identify infectious agents is an essential first step in the assessment of biothreats. However, meaningful assessment of the risks posed by an infectious agent once detected, and the implementation of an effective means to mitigate the threat requires information like antibiotic resistance, toxin production, or virulence that current analytical systems are not designed to produce. Protein analyses can provide information useful for both the phylogenetic identification of microorganisms and the assessment of physiological cell functions, which are actuated by proteins. For instance, the amino acid sequence of structural proteins (e.g., ribosomal proteins) can provide information for phylogenetic identification, while amino acid sequences of functional proteins (e.g., toxins) can provide information on virulence. Unfortunately, prior art detection and identification methods that are able to use proteomic information require long analysis times and a prior understanding of the type of infectious agent that may be present in a sample.

Accordingly, there is a need to develop methods for rapidly detecting microorganisms, particularly bacterial organisms that permits protective measures or countermeasures to be quickly implemented in the event of an attack with weapons employing the same or as a robust method of identifying the causative agent(s) in an illness outbreak. Moreover, the demand for methods and assays capable of rapidly detecting and identifying microorganisms has applications beyond those of the military such as in the pharmaceutical, medical, food and public safety industries, and the like.

SUMMARY OF THE INVENTION

A process is provided for of identifying a cell type in a sample that includes identification of one or more peptide sequences in the sample. Identification is facilitated by prior cleavage of sample protein into constituent peptide sequences. Mass spectrometry is particularly well suited for identification of peptide sequences. Each peptide sequence is assigned to a protein of known sequence. A matrix of assignments is generated for the presence or absence of each peptide in one or more cells. An exemplary matrix form includes a row vector $b_{u(1-n)}$ where n is the number of sequenced peptides from the sample and $b_u$ is the unknown sample cell type, and a column vector $b_{1-i}$ where i is the number of cell types in a database. The matrix of assignments is rearranged according to cell classification. A cell type based on the most probable cell classification is identified. When the exemplary matrix of assignments is used, a cell type is identified in the sample based on the highest number of peptide matches between row $b_u$ and row $b_i$.

DETAILED DESCRIPTION OF THE PREFERRED EMBODIMENTS

Figure 1:
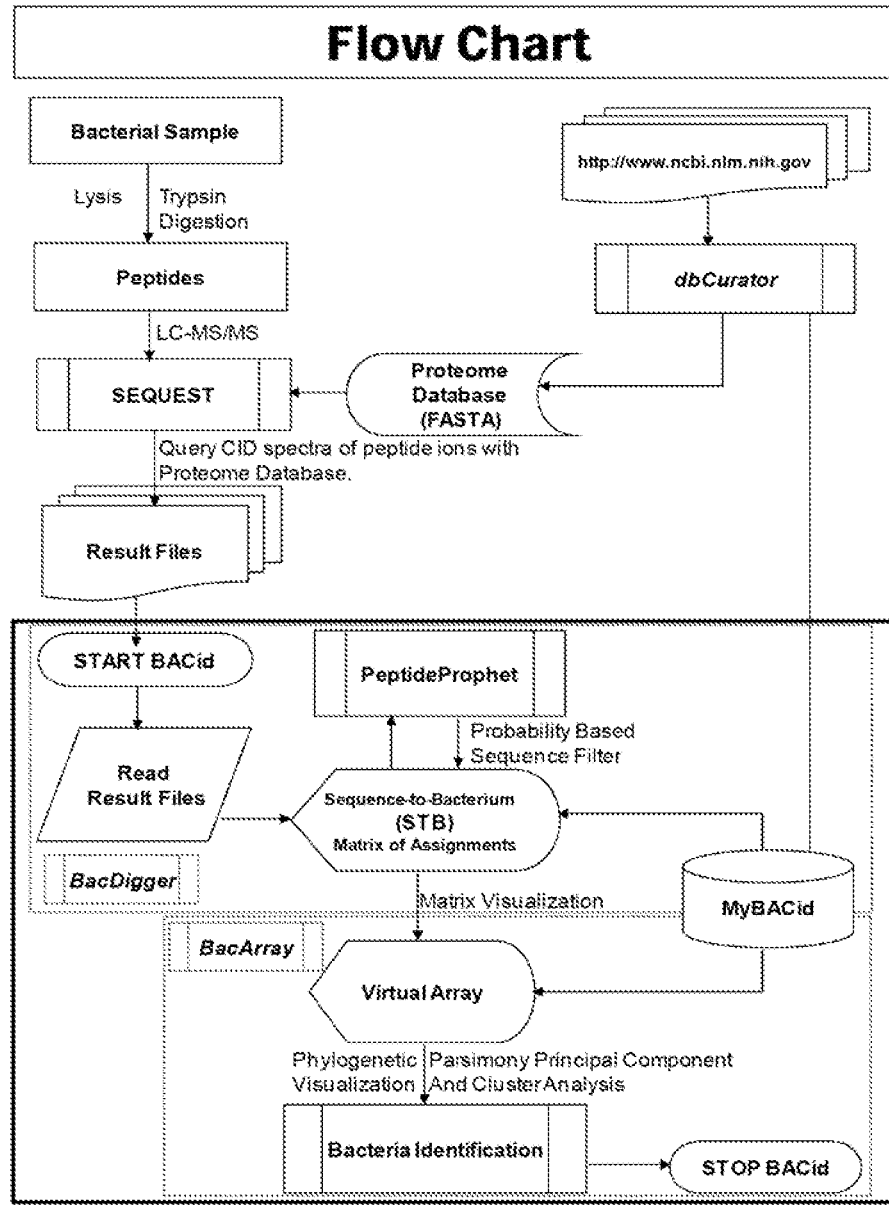
FIG. 1 is a data flow chart according to one aspect of the present invention.

Currently, more than two hundred bacteria have been fully sequenced and more than six hundred sequencing projects are in progress. Completely sequenced genomes provide amino acid sequence information of every protein potentially expressed by these organisms. They also provide information that can be used to track mutations or infectious agent genetic crossover events. The combination of the known and putative protein sequence information with mass spectrometry (MS) technologies capable of identifying and characterizing amino acid sequences of proteins and identify the presence or absence of post-translational modifications enabled the design the subject inventive procedure for the classification and identification of bacteria or other cells or viruses based on querying proteomic sequences.

To this end, gel-free proteomic procedures based on coupling liquid chromatography (LC) electrospray ionization (ESI) or matrix-assisted laser desorption/ionization (MALDI) with tandem mass spectrometry (MS/MS) analysis of peptides generated from cellular proteins is developed as an attractive technological platform for identification and classification of microorganisms. The subject invention addresses the challenging task of to translate the raw data generated from MS/MS experiments into a biologically meaningful and easy to interpret results suitable for identification and classification of microorganisms with high confidence.

A suite of bioinformatics tools is provided herein that when combined with peptide cleavage and sequence identification techniques provides rapid classification and identification of bacteria or other cell types based on the proteomic information generated from LC/MS/MS analysis of tryptic digests of bacterial protein extracts and profiling of the sequenced peptides to create a matrix of sequence-to-bacterium (STB) assignments. Using database bacteria proteomes as a reference, we developed an unsupervised approach to reveal the relatedness between the test and database microorganisms. This binary matrix is analyzed using diverse visualization and multivariate statistical techniques for bacterial classification and identification.

The relevance and consistency of this suit of algorithms, herein referred to as BACid, for the identification of bacteria is demonstrated by using an illustrative example of processing MS/MS spectra of peptide ions obtained during LC/MS analyses of a model bacterial mixture.

The current invention has utility as a means for detecting any cell type in a sample independent of whether the cell type is suspected of being present in the sample and independent of sequence mutations, insertions, deletions, or other altering genetic or protein characteristics.

As used herein, the term "sample" is defined as sample obtained from an environmental source, a biological organism, a tissue, cell, cell culture medium, or any medium suitable for mimicking biological conditions, or from the environment. Non-limiting examples include, saliva, gingival secretions, cerebrospinal fluid, gastrointestinal fluid, mucous, urogenital secretions, synovial fluid, cerebrospinal fluid, blood, serum, plasma, urine, cystic fluid, lymph fluid, ascites, pleural effusion, interstitial fluid, intracellular fluid, ocular fluids, seminal fluid, mammary secretions, vitreal fluid, nasal secretions, water, air, gas, powder, soil, biological waste, feces, cell culture media, cytoplasm, cell releasate, cell lysate, buffers, or any other fluid or solid media.

A sample is preferably a fluidic sample. Illustratively, a fluidic sample such as serum or cell lysate is diluted in a buffered saline solution suitable for activity, maintenance, lysis, or other state or requirement of a therein contained cell. Alternatively, a sample is solid wherein a suspension is created in a buffered saline solution or the solid is dissolved in a solvent such as a buffered saline solution. An illustrative example of operative buffered solutions are 50 mM Tris-HCl, 10 mM $MgCl_2$, 100 mM NaCl, pH 8.0 or 25 mM Tris/HCl, pH 7.6, 25 mM KCl, 5 mM $MgCl_2$. It is appreciated that other buffered or non-buffered solutions are similarly operable. Other buffers operable are illustratively, HEPES, Tris, phosphate, carbonate, imidizole, acetate, or any other buffer known in the art. Salts and other cations are further operable in the subject invention. (see e.g. Endo, Y, et al, *J Biol Chem*, 1987; 262:8128-30.) Preferably, magnesium ions are included in a buffer or solution. Endo, Y. *J Biol Chem*, 1988; 263:8735-8739. More preferably, magnesium is between 5 and 15 mM.

The instant inventive methods are amenable for use in diagnosis of bacterial, viral, protista, or other infection in a patient. The term "patient" as used herein refers to a single or multicellular organism illustratively including, but not limited to a, human, monkey, ape, upper and lower primates, horse, donkey, goat, rabbit, mouse, rat, guinea pig, hamster, mammals, non-mammals, and insects.

The term "nucleotide" or "nucleic acid" are used interchangeably herein and are intended to mean a base-sugar-phosphate combination either natural or synthetic, linear, circular and sequential arrays of nucleotides and nucleosides, e.g. cDNA, genomic DNA, mRNA, and RNA, oligonucleotides, oligonucleosides, and derivatives thereof. Included in this definition are modified nucleotides which include additions to the sugar-phosphate groups as well as to the bases.

The term "nucleic acid sequence" refers to multiple nucleotides attached in the form of a single or double stranded polynucleotide that can be natural, or derived synthetically, enzymatically, and by cloning methods. The term "oligonucleotide" refers to a polynucleotide of less than 200 nucleotides. The terms "nucleic acid sequence" and "oligonucleotide" may be used interchangeably in this application.

The term amino acid refers to any naturally or non-naturally occurring amino acid. An amino acid is illustratively an L- or D-amino acid, modified amino acid, glycosylated, phosphorylated, sulfated, or otherwise labeled amino acid. As the detection system is operable detect mass, the structure of an amino acid does not affect the method.

A method for the rapid and sensitive detection of unknown cell types in a sample is provided. In a preferred embodiment a sample is a biological fluid such as a nasopharyngeal secretion or serum. A sample is optionally obtained from a patient who may or may not be demonstrating symptoms of an infection. For example, a patient infected with an influenza virus may be demonstrating symptoms of fever, chills, cough, muscle aches, or other. However, these symptoms do not immediately present themselves, but require an incubation time of the infectious agent prior to symptom onset. The present invention provides for sensitive detection prior to symptom onset. Thus, a patient who is merely suspected of harboring an infectious agent or may have been exposed is a candidate for sample donation.

The inventive method is operable for detecting, identifying and distinguishing multiple cell types in a sample. Illustratively, a sample may contain two bacterial species and two viral species. The inventive process is operable for simultaneous detection of both bacterial species and optionally both viral species present in the sample. The number of cellular or other target species can be two, three, four, five, six, seven, eight, nine, ten, or more. The number of cellular or other species is optionally any number between 1 and about 100. The number of simultaneously detectable species can be any number up to the number of identifiable peptide sequences in a sample.

In order to practice the present invention, one or more mass spectra are obtained from at least one of a set of peptides ("experimental peptide") present in a sample that is to be identified or matched to a peptide sequence in a database.

In one embodiment, the experimental peptide is obtained by selective cleavage of a mixture of polypeptides, for example a mixture all polypeptides present in a sample. Alternatively, the experimental peptide is obtained by selective cleavage of a polypeptide that has been isolated free from other polypeptides. An advantage of the subject invention is that no prior isolation of protein or peptides from a sample is required. However, any level of sample processing prior to peptide sequence identification may improve detection using the inventive process. For example, lysis of red blood cells from a whole blood sample, barium precipitation, size exclusion chromatography, gel electrophoresis, or other processing technique is amenable for use with the subject inventive process.

Enzymatic cleavage is suitable to generate a family of peptides from a protein containing sample. Suitable enzymes illustratively include arginine endopeptidase (ArgC), aspartic acid endopeptidase N (aspN), chymotrypsin, glutamic acid endopeptidase C (gluC), lysine endopeptidase C (lysC), V8 endopeptidase, trypsin, endoproteinase Asp-N, endoproteinase Arg-C, endoproteinase Glu-C, endoproteinase Lys-C, pepsin, thermolysin, elastase, papain, proteinase K, subtilisin, clostripain, exopeptidase, carboxypeptidase A, B, P, or Y, cathepsin C, acylamino-acid-releasing enzyme, pyroglutamate aminopeptidase, other proteases known in the art, combinations thereof, mutants thereof, or fragments thereof. See e.g. *Cold Spring Harbor Protocols*. Proteases suitable for use in the instant invention are illustratively obtained from Sigma-Aldrich, Co. (St. Louis, Mo.). It is appreciated that other proteases are similarly suitable for use in the instant invention. Additionally, it is appreciated that other chemical means of digestion are suitable illustratively including, acid, base, or other chemical digestion methods known in the art. Other enzymes with sufficiently restrictive cleavage patterns may also be used and are known in the art. Non-enzymatic selective cleavage is also suitable, for example use of cyanogen bromide to cleave a polypeptide at the C-terminal side of Met residues.

Trypsin is a most preferred enzyme. Trypsin cleaves specifically at the carboxyl side of lysine (Lys) and arginine (Arg) residues, so that the resulting tryptic digest fragments should have a Lys or Arg as the C-terminal amino acid, unless the peptide fragment was obtained from the C-terminal end of the peptide. Similarly, the amino acid in the intact polypeptide that, prior to cleavage, directly preceded the N-terminal amino acid of the peptide fragment should also be a Lys or Arg, unless the peptide fragment was obtained from the N-terminus of the peptide.

The resulting fragments of digestion are then analyzed by a suitable, rapid, and quantitative analysis technique. Preferably, analysis is performed by liquid chromatography (LC) coupled to mass spectrometry (MS). LC techniques suitable for use in the instant invention illustratively include high-performance LC, ultra-high performance LC, and standard column or slab gel chromatography techniques. Examples of suitable columns for separation of digestion products (target or experimental peptides) illustratively include a $C_{19}$ HPLC column such as the Symmetry-300 $C_{18}$ column available from Waters, Corp. (Bedford, Mass.). It is appreciated that other column types are similarly suitable for use in the present invention. Column parameters such as inner diameter, length, number of theoretical plates, etc. are recognized in the art and persons having ordinary skill in the art readily recognize methods of optimizing these and other necessary parameters to facilitate effective separation of a single or family of target peptides. Thus, it does not require undue experimentation to adjust parameters of LC columns.

A second or other additional columns are optionally employed to further separate the target peptides. In a preferred embodiment, the elution of a $C_{18}$ reverse phase HPLC column is coupled to a chromatographic step on a Waters NanoAcquity column also available from Waters, Corp. The separated target peptides are subsequently submitted to a mass spectrometry system tor detection, identification, and quantitation.

Suitable detection and quantitation systems illustratively include electrospray, matrix assisted laser desorption ionization (MALDI), time of flight (TOF), multiple quadrupole, and other types of mass spectrometry systems known in the art. Illustratively, a Waters Q-Tof Premier TOF quadrupole tandem mass spectrometer available from Waters, Corp. or an API 4000-Q trap triple quadrupole tandem mass spectrometer (Applied Biosystems, Foster City, Calif.) are each suitable for use in the instant invention. It is appreciated that other brands and types of mass spectrometers are similarly suitable.

In one embodiment, one or more fragmentation mass spectra are obtained from the experimental peptide. Alternatively, ladder sequencing may be used to obtain one or more mass spectra as described in U.S. Pat. No. 6,271,037, which is incorporated herein by reference. Processes that produce fragmentation useful for generating a fragmentation mass spectrum, include but are not limited to, collision-induced dissociation (also known as collision-activated dissociation), post-source decay from laser desorption, surface-induced dissociation, and in-source fragmentation. Ionization processes which can be used illustratively include, without limitation, electrospray ionization, nanoflow electrospray ionization, matrix-assisted laser desorption ionization, plasma desorption ionization, fast atom bombardment, and field desorption.

A mass spectrum can be generated using tandem mass spectrometry or multiple stages of mass spectrometry. Multiple mass spectrometry platforms are suitable for use in the instant invention illustratively including matrix assisted laser desorption ionization time of flight mass spectrometry (MALDI), electrospray mass spectrometry, electrospray ionization-Fourier transform ion cyclotron resonance mass spectrometry (ESI-FTICR), multi-stage mass spectrometry fragmentation analysis (MS/MS), mass spectrometry coupled with liquid chromatography such as high performance liquid chromatography mass spectrometry (HPLC) and ultra performance liquid chromatography isotope dilution tandem mass spectrometry (UPLC-ID/MS/MS), and variations thereof.

In one preferred embodiment, a mass spectrum is obtained by linear tandem mass spectrometry, for example, using a tandem time-of-flight (TOF-TOF) mass spectrometer. Alternatively, a mass spectrum is obtained by orthogonal mass spectrometry, for example using a quadrupole tandem time of flight (Q-TOF) or Q-STAR mass spectrometer. Other instrument types and configurations can be used, provided they result in a sufficient number of the required suite of sequencing ions to generate sequence information. These include, without limitation, tandem magnetic sector instruments, Fourier-transform ion cyclotron resonance mass spectrometers, and quadrupole ion trap mass spectrometers.

In a preferred embodiment a quadrupole time of flight mass spectrometer is used with detection by multiple reaction monitoring (MRM). MRM increases both the selectivity and the sensitivity of detection system by monitoring chromatographic co-elution of multiple transitions for a given peptide.

Wolf-Yadlin, A, et al, *Pro Natl Acad Sci USA*, 2007; 104: 5860-65. MRM has been previously used for detection of doping substances (Guan, F. et al, *J Chromatogr B Analyt Technol Biomed Life Sci*, 2005; 829:56-68; Ho, EN, et al, *J Chromatogr A*, 2006; 1120:38-32; Thevis, M, et al, *Biomed Chromatogr*, 2001; 15:393-402; Herrin, (GL, et al, *J Anal Toxicol*, 2005; 29:599-606), detection of DNA adducts (Koc, H & Swenberg, J A, *J Chromatogr B Analyt Technol Biomed Life Sci*, 2002; 778:323-343), and for some proteomic studies (Wolf-Yadlin, A, et al, *Proc Nat. Acad. Sci USA*, 2007; 104: 5860-65; Kirkpatrick, DS et al, *Methods*, 2005; 35:265-273; Liao, H, et al, *Arthritis Rheum*, 2004; 50:3792-3803).

The mixture of peptide fragments (experimental peptides) obtained from digestion of individual polypeptides (or mixtures of polypeptides) can be analyzed by mass spectrometry without any prior separation or can optionally be separated into individual experimental peptides using known chromatographic methods. In a preferred embodiment, the experimental peptides are separated by liquid chromatography and direct injected into a tandem quadrupole mass spectrometry system for identification of parent mass and sequence. Accurate measurement of peptide masses in the primary mass spectrum advantageously increases the specificity of the mass-constrained database searches used in subsequent steps of a preferred embodiment of the present invention. Other mass spectrometric techniques capable of mass measurement within an error of 100 ppm or less include, without limitation, time-of-flight, Fourier transform ion cyclotron resonance, quadrupole, ion trap, and magnetic sector mass spectrometry and compatible combinations thereof.

In order to determine a peptide sequence within the experimental peptide, a fragmentation spectrum for the corresponding parent ion is obtained. Preferably, the fragmentation mass spectrum is obtained for a parent ion having m/z greater than or equal to 400, e.g. as determined in a primary mass spectrum. Tandem mass spectrometry may be carried out on a doubly protonated parent ion ($[M+2H]^{+2}$), although the method can be performed on parent ions of other charge states, e.g. $[M+H]^+$ or $[M+3H]^{+3}$.

In one preferred embodiment, a Q-TOF mass spectrometer is used with the quadrupole mass analyzer set to allow transmission of ions with an m/z equal to that of the doubly protonated peptide ion ($[M+2H]^{+2}$) deduced from the singly charged peptide ion ($[M+H]^+$) observed in a primary mass spectrum. The transmitted ions are termed 'parent' or 'precursor' ions. The peptide ion beam passes into the collision cell where the parent ions are subjected to low energy CID. This can be achieved through the application of a voltage on the collision cell and/or by the introduction of an inert gas. The resulting fragment ions (termed the 'product' or 'daughter' ions) and any intact parent ions are then transmitted into the TOP mass analyzer. The predominant ion series results from cleavage across the peptide backbone, and gives rise to a, b and y ions. In another preferred embodiment employing a TOF-TOF mass spectrometer, the timed ion selector is preferably set to capture ions in a high energy collision cell at m/z equal to that of the singly charged peptide ion ($[M+H]^+$). In this case, fragmentation occurs both across the peptide backbone, giving rise to N-terminally charged ions (a, b and c ions) and C-terminally charged ions (x, y and z ions), and also across the side chains, giving rise to d and w ions. Fragmentation (MS/MS) spectra are typically represented by a two-dimensional graph with ion intensity on the y-axis, and mass-to-charge ratio (m/z) on the x-axis.

It is appreciated that numerous other detection methods are similarly suitable for detecting a peptide. Illustrative examples include, but are not limited to, liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, or combinations thereof.

A protein database is constructed optionally in a FASTA format using annotated bacterial proteome sequences derived from fully sequenced chromosomes of any target species illustratively including bacteria, including their sequenced plasmids. The description herein is illustratively targeted to detection and identification of bacterial species. It is appreciated that the method is similarly operative to detect any organism, cell type, virus, protein, or peptide independent of modification, mutation, weaponization, or other alteration.

The identified sequences in the sample are then compared to the known or putative sequences present in the constructed databases using. BACid. BACid contains a suite of algorithms (modules) developed using Microsoft Visual Basic (VB) .NET and PERL to analyze bacterial similarities and their identification from a virtual array of STB matrix of assignments. A data flow chart is shown in FIG. 1.

The first module (dbCurator) written in Perl downloads the microorganism sequences and edits the header information of each protein optionally from the National Institutes of Health National Center for Biotechnology (NCBI) website. Each database protein sequence is optionally supplemented with information about a source organism and a genomic position of the respective ORF embedded into a header line. This new theoretical proteome of a microorganism is appended in a flat file that is saved as FASTA format. dbCurator also updates the in-house microorganism relational database (MyBACid) created using MySQL with the microorganism information like name, strain, sequencing center, and other available data related to each bacterium. BACid optionally utilizes two databases; the flat file FASTA format database used as the reference and MyBACid, which is a central repository database. The Perl package manager available with ActivePerl is used to install the Perl DBI (database interface) and the MySQL database driver from CPAN.

The database of bacterial proteomes is constructed by translating 607,616 putative protein-coding genes (as of Jun. 20, 2005) and consists of 38,252,355 amino acid sequences of potential tryptic peptides obtained by the in silico digestion of all proteins (assuming up to two missed cleavages). The database is continually updated with each new genomic, gene, or protein sequence available. The experimental MS/MS spectral data of bacterial peptides are searched by a SEQUEST algorithm against this protein database. Eng, J. K., et al. *J. Am. Soc. Mass. Spectrom.*, 1994; 5:976-989.

The second module (BacDigger) is designed to analyze the SEQUEST output files. The function of this module is to retrieve sequence matches to the in-house reference bacterial proteomes based on the identity of the peptides determined by SEQUEST and to obtain values for the matching parameters like cross correlation ($X_{corr}$) value normalized score $\Delta C_n$, preliminary score ($S_p$), rank of the preliminary score ($RS_p$), absolute value of the mass difference $\Delta M$, and number of amino acids in the peptide sequence identified. Assigning each peptide sequence a probability score determined by running PeptideProphet algorithm developed at Institute of Systems Biology validates the SEQUEST peptide sequence assignment. Keller, A., et al., *Anal. Chem.*, 2002; 74:5383-5392. Using the information contained in the reference of each output file from each identified peptide by mass spectrometry, a STB binary matrix of assignments is created. This matrix of assignments, generated using raw results, is archived in a comma separated file format (CSV) for audit.

Based on probability values, determined by a PeptideProphet algorithm that a sequence was correctly identified, a user specified threshold is applied to elements of the STB matrix of assignments to filter out low probability matches. This new 'extracted' STB matrix of assignments is also saved in a CSV format. In addition, BacDigger optionally removes duplicate sequences from the data set and retains only a unique set of peptides.

A matrix of assignments comprises one or more rows and one or more columns. Row vector $b_{u(1-n)}$ represents the sequencing information from the unknown cell(s) in the sample where $b_u$ is the unknown sample cell type and n is the number of sequenced peptides from the sample. Column vector $b_{1-i}$ represents a plurality of row vectors each representing the sequence information for a cell type in the database where i is the number of cell types in the database. Each position in each row is labeled with information indicating whether the particular protein or peptide in any given cell type i is present in the unknown cell type(s) in the sample $b_u$.

The inventive process preferably arranges the known database cells $b_{1-i}$ into super-proteomes. A super-proteome is illustratively a family of phylogenetically associated cell types or proteomes. Illustrative examples of a super-proteome is the firmicutes proteome represented in FIG. 2C and the proteobacteria proteome of FIG. 2D. The arrangement of the database cells into super-proteomes provides rapid and user-friendly identification of unknown cells based on nearest phylogenetic match. This method provides a researcher or investigator with the ability to identify new, previously unknown cell types from a sample without the need for detailed sequence information prior to sample analysis.

The third module (BacArray) takes the STB matrices of assignments and optionally displays numerical values in the form of color bitmaps ('virtual arrays'). During this process, BacArray rearranges assignments by grouping database bacteria according to their taxonomic positions by using the relevant information stored in MyBACid. This allows for interactive browsing of sequence assignments, which can be further validated as they are dynamically linked with NCBI protein databases for blasting the sequences of interest.

The BacArray communicates with external statistical libraries to apply multivariate statistical techniques like principal component and cluster analysis to the STB matrices of assignments. In addition, it generates combined reports of such analyses, thus, enabling the module to display the most probable taxonomic position of studied microorganisms and provides a user friendly display of results.

An inventive process uses the aforementioned techniques and analysis tools to detect and identify a cell type, organism type, protein, or peptide. If an organism is not represented in the database such as it being a previously unidentified strain of bacteria or a virus, the inventive process successfully identifies its phylogenetic nearest neighbors allowing for classification and predictive characteristics of the previously unknown organisms. Illustratively, an unknown bacterial agent is developed and weaponized. The inventive process can identify what source bacterial or other organism was used to construct the weaponized bacterial agent. This provides researchers with essential information about how to best isolate, treat, or combat the unknown bacterial agent.

An inventive process as described herein illustratively includes providing a sample. Using one or more techniques to identify one or more peptide sequences as a component or the only content of the sample. The identified peptide sequence is assigned to a protein of known or putative sequence. A matrix of assignments is generated for the presence or absence of each of the plurality of peptides in one or more cells. Optionally, the matrix is rearranged according to cell or organism phylogenic classification and the unknown sample cell is identified based on either an exact match or the most probable cell classification.

The inventive process further illustratively includes generating one or more databases comprising a plurality of cellular proteome sequences and optionally other identifying information.

As a method of filtering out weak matches a probability score is optionally assigned to each peptide/protein match. A user or machine generated threshold value is used to select sequences with the desired level of confidence in sequence match. Optionally, these matched proteins are further filtered to remove sequences that are ubiquitous throughout the database and provide little or no identifying propensity. These methods simplify the subsequent comparisons and increase the confidence in the detection or identification of an unknown cell in a sample.

Ancillary reagents are any signal producing system materials for detection of an unknown cell, protein, or peptide in any suitable detection process such as ELISA, mass spectrometry, western blot, immunoprecipitation, HPLC, UHPLC, or other process known in the art.

The invention is operable in both a field and laboratory setting. A sample is optionally obtained at a location remote from the site of analysis. Illustratively, a physician's office, hospital, site of biological weapon deployment, infectious hot zone, source of contamination or other site of interest.

In a preferred embodiment, a diagnostic kit is provided that illustratively includes a microtiter plate or other support or chamber such as an collection tube sealable or not sealable, control sample containing known cell type(s), buffer, swab or other sample collection devices, control reagents such as competing or unlabelled reagents, control substrate and reagents, protease inhibitors, or other necessary or desired reagents. The kit optionally includes instructions printed or in electronic form and customer support contact information.

The components of the kit are any of the reagents described above or other necessary and non-necessary reagents known in the art for solubilization, detection, washing, storage, or other need for in a diagnostic assay kit.

The current invention will quickly and conveniently determine if an unknown sample possesses a biological threat agent such as a cell or spore and will greatly aid in triage of victims following suspected exposure to a biological agent such as anthrax. In addition, the invention will aid in initial forensic investigation by immediately determining potency at any remote location. As such, field forward personal will make estimates of purity/grade and the age of the weapon at the site of dispersal and with rapid and sensitive results. The inventive rapid screening assay to assess cell type will also prove beneficial to the pharmaceutical or academic research industries as a screening tool for genetically engineered or accidentally occurring cells.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to mammalian cells, tissue, fluids, or subjects, a person having ordinary skill in the art recognizes that similar techniques and other techniques know in the art readily translate the examples to other mammals such as humans. Reagents illustrated herein are commonly cross reactive between mammalian species or alternative reagents with similar properties are commercially available, and a person of ordinary skill in the art readily understands where such reagents may be obtained.

EXAMPLE 1

Bacterial cells (*Escherichia coli* K-12 and *Bacillus cereus* ATCC 14579) are grown and processed before LC-MS analysis as described by Dworzanski, J. P., et al., *Anal. Chem.*, 2004; 76:2355-2366. The sample is subjected to trypsin digestion of their cellular proteins to generate a representative set of peptides. Detectable peptides are subjected to analysis using reversed phase liquid chromatography (LC) coupled with an electrospray ionization mass spectrometry system (LCQ DECA Surveyor, ThermoFinnigan, San Jose, Calif.). Each MS data acquisition cycle consists of a full-scan MS over the mass range 400-1400 m/z, followed by three data-dependent MS/MS scans over m/z 200-2000 on the three most intense precursor ions from the survey scan.

MS/MS spectra of peptide ions generated during the electrospray ionization process of tryptic peptides derived from bacterial proteins are searched against a preconstructed protein database with SEQUEST and the output files are processed by BACid (FIG. 1). Amino acid sequences of peptides are validated using probability scores generated by PeptideProphet and a set of 289 accepted peptide sequences (P>0.98) are considered as elements of a row vector $b_u$ that represents the peptide profile of unknown (u). Accordingly, sequence-to-bacterium (STB) assignments $a_{1i}$ are elements of a row vector $b_1$ that represents a peptide profile of a database bacterium assigned as number 1, and in general assignments $a_{ij}$ are elements of row vectors $b_i$, where i represents the theoretical proteome of a $i^{th}$ bacterium in the database (i=1, 2, 3, ..., 203). All these row vectors form a matrix of assignment $A_{(m+1) \times n}$ that is visualized in FIG. 2A as a virtual array of n=289 peptide sequences assigned to m=202 theoretical proteomes of database bacteria and an unknown microorganism (or their mixture). Conversely, each column vector represents a phylogenetic profile $s_j$ of a peptide sequence. Thus for each MS/MS analysis, a binary matrix of assignments A is created with entries representing the presence or absence of a given sequence in each theoretical proteome of database microorganism. Similar b profiles indicate a correlated pattern of relatedness that in the majority of cases reflects the presence of identical sequences among orthologs or other functional gene segments. The method predicts that peptide sequences $b_u$, derived from cellular proteins of an unknown bacterium u, are most likely to be similar or even identical with a reference database bacterial strain $b_i$ represented by a vector $b_j$ with a highest number of non-zero elements.

The STB matrix of assignments is analyzed by computing sequence assignments to merged proteomes that comprise bacteria grouped into 'super-proteomes' of 13 phyla represented in the database. The results shown in FIG. 2B indicate that 98 unique sequences are assigned to the phylum *Proteobacteria* while 99 are assigned to *Firmicutes*. These data confirming the presence of a mixture of bacteria and allow the classification of each organism on the phylum level. The STB assignment sub matrices are further analyzed separately and the results obtained are shown in FIGS. 2C and D as dendrograms representing results of cluster analyses that are accompanied by bar graphs that visualize peptide profiles of the test samples ('unknown') and the most similar database strains revealed by cluster analysis.

Hierarchical clustering is performed using furthest neighbor (complete) linkage with squared Euclidean distances as the similarity metric and was used as an exploratory tool to examine relationships of a test microorganism with the database bacteria. Cluster analyses are performed automatically by linking STA Cluster library from Statistica (StatSoft, Inc., Tulsa, Okla.) to the BacArray module.

Figure 2:
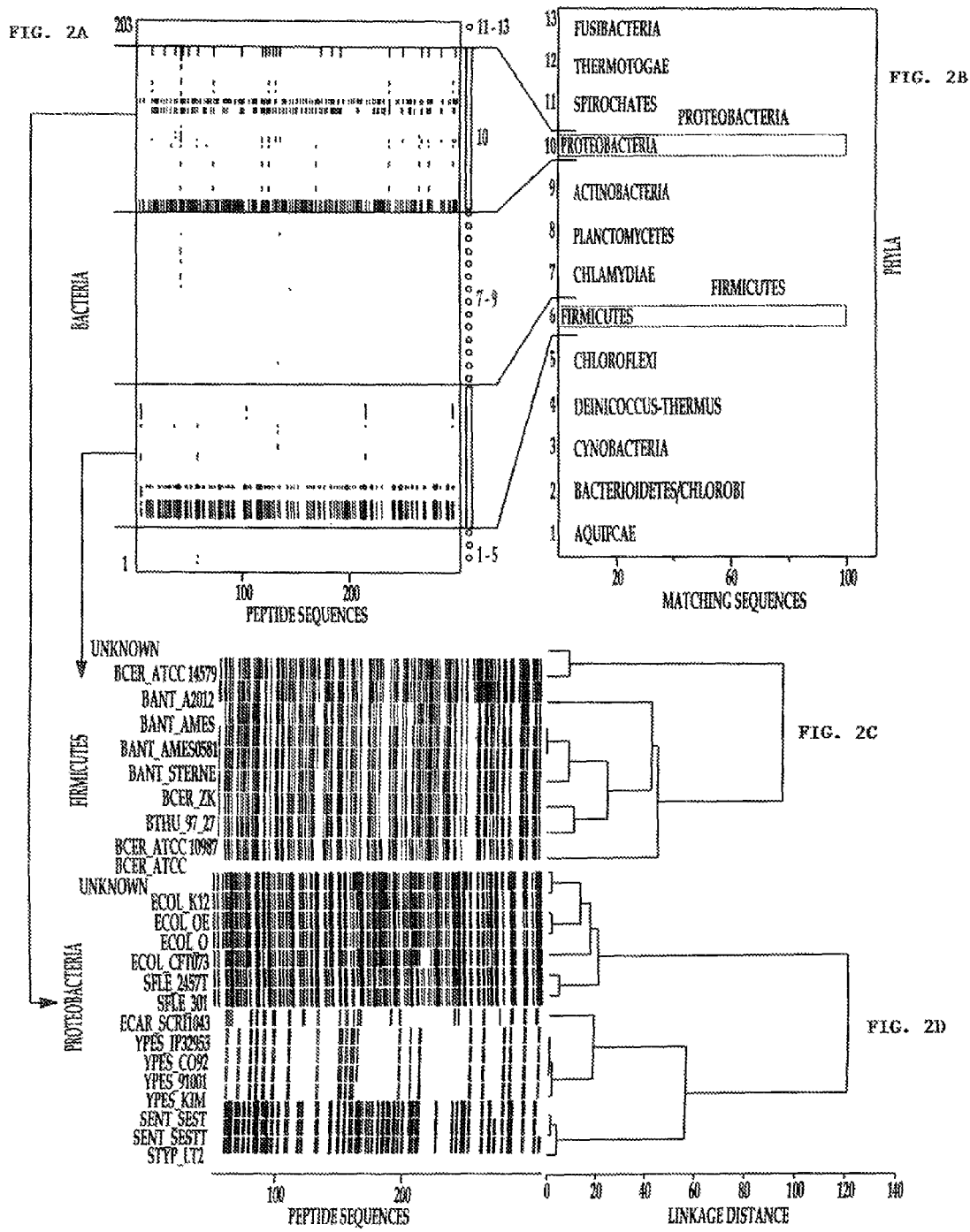
FIG. 2A depicts an output from the chart of FIG. 1 as row vectors forming a matrix of assignment $A_{(m+1) \times n}$.
FIG. 2B is a sequence-to-bacterium (STB) matrix of assignments analyzed by computing sequence assignments for a sample to merged proteomes that comprise bacteria grouped into 'super-proteomes' of 13 phyla represented in the database and indicate that 98 unique sequences are assigned to the phylum *Proteobacteria* while 99 are assigned to *Firmicutes*
FIG. 2C is a dendrogram from the sample revealing two main clusters of proteins: the first cluster groups the 'unknown' with a database strain *B. cereus* ATCC 14579; the second cluster comprises diverse *Bacillus* strains classified as *B. cereus, Bacillus anthracis* and *Bacillus thuringiensis*.
FIG. 2D is a dendrogram from the sample revealing a subcluster with a database *E. coli* K-12 strain because they differ by only two peptide sequences.

FIG. 2C reveals two main clusters: the first cluster groups the 'unknown' with a database strain *B. cereus* ATCC 14579; the second cluster comprises diverse *Bacillus* strains classified as *B. cereus, Bacillus anthracis* and *Bacillus thuringiensis*. In FIG. 2D the test sample forms a subcluster with a database *E. coli* K-12 strain because they differ by only two peptide sequences. This subcluster is grouped with other *E. coli* and *Shigella flexneri* strains into a cluster that is substantially different in comparison to the next closest cluster that comprises *Salmonella* and *Yersinia* strains.

The results of applying BACid for analysis of a bacterial sample composed of a mixture of *E. coil* K-12 and *B. cereus* ATCC 14579 strains demonstrate that mass spectrometry based proteomic approach, combined with BACid for analysis SEQUEST output files, allows for automated assignment of analyzed organisms to taxonomic groups. Moreover, BACid reveals genome-traced relatedness between bacteria that is suitable for fast and reliable classification and even identification of bacteria up to the strain level. Therefore, the application of this algorithm for analyses of proteomics data constitutes a new method that may function as a strong complement to DNA based approaches of comparing bacterial genomes.

EXAMPLE 2

Detection of Cancerous Cells in a Sample Tissue

A database is constructed based on known protein profiling of a particular or multiple tumor types in multiple tissues using dbCurator a described in Example 1. The database contains proteomic information for tumor cells from brain gliomas and normal brain tissue. Proteomic information for the database is obtained essentially as described in WIPO Patent Application WO/2007/008647 the contents of which are incorporated herein by reference. The database includes known information with respect to protein levels, the presence or absence of posttranslational modifications such as phosphorylation, sulfation, methylation, and alkylation representative of each protein in a cancerous or non-cancerous state. The inventive method functions to identify the presence of tumor cells even below otherwise detectable levels by traditional techniques.

An unknown sample is collected from the surgical margin of a resected glioma tumor and immediately snap-frozen in liquid nitrogen, and stored at −80° C. until analysis. For analysis, the tissue is homogenized in T-PER extraction buffer (50 mg of tissue per 1 mL of T-PER) in an ice-chilled Duall homogenizer and centrifuged at 16,000 x g for 30 min at 4° C. The supernatant is collected for protein identification.

Proteins with the samples are separated by ion exchange chromatography followed by reverse-phase high-performance liquid chromatography (HPLC). The supernatant is separated by anion exchange chromatography using a HiTrap Q HP anion exchange column (Amersham Biosciences, Uppsala, Sweden) and a NaCl gradient (0.05 M, 0.1 M, 0.15 M, 0.2 M, 0.25 M, 0.3 M, 0.35 M, 0.45 M, 0.55 M, and 1 M NaCl) based on the extraction solution. HPLC separation for selected fractions is achieved over a Vydac (Hesperia, Calif.) 214MS52 reverse phase C4 column (5 μm particles, 2.1 mm×25 cm) at 40° C. using a linear gradient of 5% B to 20% B over 11 min, 20% B to 30% B over 15 min, 30% B to 55%

B over 90 min, and 55% B to 95% B over 10 min. For fraction separation, solvent A is 0.1% TFA and solvent B was 0.1% TFA in acetonitrile.

Alternatively, the tissue sample supernatant is separated by cation exchange chromatography using a. HiTrap SP HP cation exchange column (Amersham Biosciences, Uppsala, Sweden) with a linear gradient of 0% B to 100% B over 15 min, where A is 10 mM ammonium acetate and B is 1 M NaCl in 10 mM ammonium acetate, pH 3.8 at room temperature. Selected fractions are separated over a Vydac (Hesperia, Calif.) 214MS5115 reverse phase C4 column (5 μm particles, 1 mm×15 cm) at 40° C. using a linear gradient of 5% B to 25% B over 5 min, 25% B to 60% B over 50 min, and 60% B to 95% B over 20 min.

HPLC fractions of interest are reconstituted in 0.1 M ammonium bicarbonate and digested with trypsin (1:50, trypsin:protein), w/w; 37° C.; 16-20 hours). Digested fragments are analyzed using either an Applied Biosystems 4700 MALDI TOF/TOF mass spectrometer (Foster City, Calif.) or a ThermoLTQ ion trap mass spectrometer equipped with to Thermo Surveyor LC pump and a microelectrospray source (Thermo Electron, San Jose, Calif.).

Analysis on the ThermoLTQ mass spectrometer is performed using one full MS scan followed by three MS-MS scans of the three most intense ions. MS/MS spectra are searched against the above constructed database using SEQUEST (Thermo Electron, San Jose, Calif.) and the Sequest search outputs are filtered using BacDigger with the following filtering criteria: cross correlation ($X_{corr}$) value of >1.0 for singly charged ions, >1.8 for doubly charged ions, and >2.5 for triply charged ion. In addition, a RSp (ranking of preliminary score) value of <5 and a Sp value (preliminary score) >350 are used for positive peptide identifications. A minimum of two peptide matches and a positive correlation between the m/z ratio detected and the MW of the intact protein (including post-translational modifications) is also used for protein identification.

Six proteins are indicative of glioma grade and predictive of survival outcome as presented in WIPO Patent Application WO/2007/008647 including: calcyclin (m/z 10092), dynein light chain 2, calpactin I light chain, astrocytic phosphoprotein PEA-15, fatty acid binding protein 5, and tubulin-specific chaperone A. Calcyclin, calpactin I light chain, and tubulin-specific chaperone A are overexpressed in grade IV gliomas. Astrocytic phosphoprotein PEA-15 is overexpressed in grade II and grade III tumors as opposed to grade IV gliomas and fatty acid binding protein 5 is overexpressed in grade III tumors as opposed to grade IV. Calcyclin and dynein light chain 2 also discriminate between glioma survival subgroups with calcyclin predominant in STS patients and dynein light chain 2 overexpressed in LTS patients.

BacID identified the presence of Astrocytic phosphoprotein PEA-15 as compared to normal neuronal tissue indicating the presence of a grade II-III glioma cell in the collected sample.

EXAMPLE 3

Identification Infectious Agents Responsible for Colony Collapse Disorder

The inventive process successfully identifies *Nosema ceranae* (Microsporidia), an emerging pathogen of *Apis mellifera*, and Israeli acute paralysis virus (IABC) as a causative agent (s) in colony collapse disorder (CCD). (See e.g. Higes, M., et al., *Environ. Microbiol. Reports*, 2009: 1(2):110-13 and for source of sample etc.)

Samples of adult bees and combs are collected from migratory beekeeping operations experiencing CCD essentially as described in Cox-Foster, DL, et al., *Science*, 2007; 318:283-87 and incorporated herein by reference. Samples of approximately 300 adult bees are collected in 70% ethanol; approximately 150 adult bees were frozen on dry ice and stored at −80° C. until processed. For analysis, the bees are homogenized in I-PER extraction buffer (50 mg of tissue per 1 mL of I-PER (Pierce, Rockford, Ill.) in an ice-chilled Duall homogenizer and centrifuged at 16,000 x g for 30 min at 4° C. to remove cellular debris and insoluble protein. The supernatant is collected for protein identification.

The soluble proteins in the supernatant are digested with trypsin (1:50, trypsin:protein, w/w; 37° C.; 16-20 hours). Digested fragments are analyzed using a ThermoLTQ ion trap mass spectrometer equipped with a Thermo Surveyor LC pump and a microelectrospray source (Thermo Electron, San Jose, Calif.) using one full MS scan followed by three MS-MS scans of the three most intense ions. MS/MS spectra are searched against a pre-constructed database of fungal and viral sequences using SEQUEST (Thermo Electron, San Jose, Calif.). The Sequest search outputs are filtered using BacDigger with the following filtering criteria: cross correlation ($X_{corr}$) value of >1.0 for singly charged ions, >1.8 for doubly charged ions, and >2.5 for triply charged ion. In addition, a RSp (ranking of preliminary score) value of <5 and a Sp value (preliminary score) >350 are used for positive peptide identifications. A minimum of two peptide matches and a positive correlation between the m/z ratio detected and the MW of the intact protein (including post-translational modifications) is also used for protein identification.

The procedure identifies *N. ceranae* in 100% of effected colonies and 85.7% of non-effected colonies. IAPV was found in 83.3% of effected colonies and only 1 (4.8%) of non-effected colonies yielding a positive predictive value of 96.1% and a specificity of 95.2%.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

We claim:

1. A process of identifying a cell type in a sample, comprising:
    identifying one or more peptide sequences in said sample on a mass spectrometer;
    assigning each peptide to a protein of known sequence;
    generating a matrix of assignments for a presence or absence of each peptide in one or more cells;
    rearranging said matrix of assignments according to cell classification; and
    identifying the cell type based on the most probable cell classification.

2. The process of claim 1 further comprising:
    generating a database of as plurality of cell proteomes.

3. The process of claim 2 wherein said assigning is performed by searching said database with said one or more peptide sequences.

4. The process of claim 1 further comprising:

assigning as probability score for each assignment of a peptide to a said protein of known sequence.

5. The process of claim 1 further comprising:
filtering out low probability assignments to said a protein of known sequence by applying a user defined threshold.

6. The process of claim 1 wherein said identifying is by liquid chromatography, mass spectrometry, liquid chromatography/mass spectrometry, static fluorescence, dynamic fluorescence, high performance liquid chromatography, ultra-high performance liquid chromatography, enzyme-linked immunoadsorbant assay real-time PCR, or combinations thereof.

7. The process of claim 6 wherein said mass spectroscopy is liquid chromatography/mass spectrometry, liquid chromatography/mass spectrometry/mass spectrometry, ultra-high performance liquid chromatography mass spectrometry/mass spectrometry, Matrix-assisted laser desorption/ionization (MALDI) mass spectrometry/mass spectrometry, or Biological Aerosol Mass Spectrometry.

8. The process of claim 1 wherein said sample is saliva, gingival secretion, cerebrospinal fluid, gastrointestinal fluid, mucous, urogenital secretion, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, nasal secretions, throat or nasal materials, feces, water, buffered saline, soil, air, or combinations thereof.

9. The process of claim 1, wherein said cell is selected from the group consisting of bacteria, archeabacteria, spore, protista, plant, virus, viral capsid, fungi, eukaryotic cell, blood cell, cancer cell, neuronal cell, or epithelial cell.

\* \* \* \* \*